United States Patent [19]
Kitajima et al.

[11] 3,937,798
[45] Feb. 10, 1976

[54] METHOD OF CONTROLLING HYDROGEN ION CONCENTRATION BY MICROCAPSULES

[75] Inventors: Masao Kitajima; Asaji Kondo, both of Saitama, Japan

[73] Assignee: Fuji Photo Film Co., Ltd., Kanagawa, Japan

[22] Filed: Aug. 17, 1971

[21] Appl. No.: 172,535

[30] Foreign Application Priority Data
Aug. 17, 1970 Japan.............................. 45-71962

[52] U.S. Cl. ................. 423/659; 423/265; 423/274
[51] Int. Cl.² ............................................. C02B 1/30
[58] Field of Search ........... 423/659, 274, 266, 265, 423/477, 478, 299; 23/253 TP

[56] References Cited
UNITED STATES PATENTS

| | | | |
|---|---|---|---|
| 714,960 | 12/1902 | Smith et al............................ | 423/274 |
| 3,014,783 | 12/1961 | Young .................................. | 423/274 |
| 3,691,090 | 9/1972 | Kitajima et al. ..................... | 252/316 |
| 3,703,576 | 11/1972 | Kitajima et al. ..................... | 424/35 |
| 3,714,065 | 1/1973 | Kitajima et al. ..................... | 252/316 |

OTHER PUBLICATIONS

"Modern pH and Chlorine Control" by W. A. Taylor & Co., Baltimore, Md., pp. 2, 6, 9, 11, 14 and 15.

*Primary Examiner*—Edward Stern
*Attorney, Agent, or Firm*—Sughrue, Rothwell, Mion, Zinn & Macpeak

[57] ABSTRACT

A method for controlling the hydrogen ion concentration of an aqueous solution is provided, which method comprises adding to an aqueous solution, microcapsules prepared by encapsulating an acid material with a polymer, which is dissolved in or swelled with water in an alkaline state only, and/or microcapsules prepared by encapsulating an alkaline material with a polymer, which is dissolved in or swelled with water in an acid state only, and adding an aqueous acid solution or an aqueous alkaline solution to the system.

17 Claims, 2 Drawing Figures

METHOD OF CONTROLLING HYDROGEN ION CONCENTRATION BY MICROCAPSULES

The present invention relates to a method of controlling hydrogen ion concentration of an aqueous solution by use of microcapsules to maintain a constant hydrogen ion concentration regardless of the variation in the composition of the solution. More particularly, the invention relates to a method of controlling a hydrogen ion concentration of an aqueous solution by use of microcapsules prepared by encapsulating an acid material with a so-called alkali-soluble polymer, i.e., a polymer soluble in water in only an alkaline state, or microcapsules prepared by encapsulating an alkaline material with a so-called acid-soluble polymer, i.e., a polymer soluble in water in only an acid state.

2. Description of the Prior Art

In a chemical reaction by use of an aqueous solution, it frequently happens that the hydrogen ion concentration of the aqueous solution must be maintained at a constant value, and for the purpose a pH buffer solution is usually used. As such buffer solution, there are known Kolthoff's buffer solution, Sorensen's buffer solution, Clark-Lub's buffer solution, McIlvanes's buffer solution, and Walpole buffer solution, which are mixtures of aqueous solutions of weak acids or weak alkali and the salts of them. However, if it is desired to increase the buffering power of the buffer solution, the concentration of the salt must be increased, which makes it improper to use such buffer solution in a a reaction system which will form precipitations by the presence of the salt or in an enzyme reaction which will delicately be influenced by the concentration of the salt.

For overcoming such difficulties, there have been proposed buffer solutions prepared by using compound each having an atomic group showing various dissociation characteristics in the one molecule. Among them a buffer solution containing tris-hydroxymethylaminomethane as the main component, i.e., a so-called tris buffer solution is used frequently for particularly biochemical experiments. However, the buffer solution is expensive and then it is improper to use such solution in a large amount.

SUMMARY OF THE INVENTION

The capsules for the buffer solution of this invention are based on a new principle quite different from the principle of buffer solution. That is to say, the buffer action in this invention occurs by such mechanism that when the capsules for buffer solution by the present invention are dispersed in an aqueous reaction system, they are maintained in an ordinary dispersion system, and no materials are dissolved in the aqueous phase in the original state, but when the pH of the reaction system is varied by the addition of an acid or an alkali to the reaction system, an alkali or an acid in the capsules is released in the reaction system in such amount as necessary for compensating the variation of the pH, whereby the pH of the reaction system is maintained at a constant value. Accordingly, in the initial stage of the reaction, the concentration of the salts and the buffer reagent in the reaction solution are substantially zero and hence the capsules give no bad influences on the reaction.

Also, in the capsules for the buffer solution by the present invention, the buffering range may be preliminary determined by the properties of the core material and encapsulating materials and the diameter of the capsules regardless of the amount of the capsules. Therefore, at the use of such capsules, it is unnecessary to measure or control the amount of the capsules to be added, i.e., a proper amount of the capsules may be added to the reaction system. Moreover, the capsules may be added to the reaction system during the progress of the reaction, which makes the handling of the capsules profitable remarkably compared with conventional buffer solutions. Furthermore, the capsules can be readily removed from the reaction system if necessary.

BRIEF DESCRIPTION OF THE DRAWINGS

The invention is described by referring to the drawing, in which.

DETAILED DESCRIPTION OF THE DRAWINGS

Figure 1:
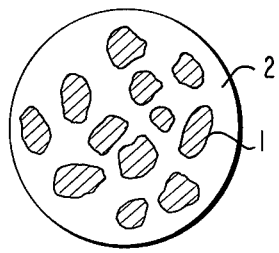
FIG. 1 is a schematic cross sectional view of a microcapsule for pH buffer solution by the present invention and FIG. 2 is a graph showing the variation of the pH of distilled water having dispersed therein oxalic acid-containing microcapsules of cellulose acetate phthalate when aqueous sodium hydroxide solution is added to the aqueous dispersion.

As shown in FIG. 1 which shows an embodiment of the microcapsule used in the invention, a solid acid powder 1 is encapsulated closed by a polymer shell 2 which is dissolved in only an alkaline solution and consitutes also the continuous phase of the capsule. Because the polymer shell of the capsule is non-permeable for a neutral solvent or an acid solvent, the encapsulated material is not diffused into such a kind of solvent or solution. However, if the solution is alkalified by a reaction product or an additive added to the solution afterward, the capsule shell is attacked by the solution and swelled to increase the permeability of the shell and thus a part of the acid within the capsule is released into the solution to neutralize it. When the solution is neutralized by such mechanism, the permeability of the capsule shell is reduced to control the release of the excessive amount of the acid in the solution. In such manner the pH of the solution is maintained at a constant value unless an alkali is not freshly added to the solution.

In case of buffering a solution under reaction from being carried into an acid state during reaction, capsules prepared by encapsulating an alkali with an acid-soluble polymer are used. The buffering action of the capsules to acid will be understood by the above-mentioned case of the acid-containing capsules.

By adding both of the acid-containing capsules and the alkali-containing capsules in a solution, a stable solution is obtained showing buffering actions in any case where the variation of the pH of the system is caused by acid or alkali.

DETAILED DESCRIPTION OF THE INVENTION

Now, the materials used in this invention will be explained hereinafter. As the core materials to be encapsulated, any inorganic or organic strong acid or week acid and alkaline materials may be utilized. For instance, the acids used in this invention include sulfuric acid, hydrochloric acid, nitric acid, sulfamic acid, formic acid, phosphoric acid, oxalic acid, succinic acid, citric acid, etc., and the alkalis used in this invention include sodium hydroxide, potassium hydroxide, sodium carbonate, sodium bicarbonate, n-dibutylamine, di-potassium phosphate, di-sodium phosphate and trihydroxymethylamino-methane, etc. Sodium phosphate and potassium phosphate may also be employed as the acid material in this invention.

As the polymers for shells of microcapsules, polymers showing specific solubility and swellability in a specific hydrogen ion concentration are used. As the polymer for capsule shell containing acid, so-called alkali-soluble polymers are used.

Examples of the polymers include cellulose derivatives such as cellulose acetatephthalate, ethylhydroxyethyl cellulose hydroxypropyl methyl cellulose phthalate and the like; starch derivatives such as starch acetatephthalate and the like; a vinylic copolymer of a vinyl monomer such as vinyl acetate, vinylbutyl ether, and styrene and maleic anhydride; acrylic copolymers such as methyl acrylate-methacrylic acid copolymer, styrene-acrylic acid copolymer, and the like; and di-basic acid monoesters such as polyvinyl acetatephthalate and the like.

A compound having a property of being swelled by alkali, such as shellac, casein resin, etc., may also be used as the alkali-soluble polymers in this invention.

As the polymers for capsule shells containing alkali therein, so-called acid-soluble polymers are used in this invention.

Examples of such polymers include cellulose derivatives such as diethylaminomethyl cellulose, cellulose acetate N,N-di-n-butyl-aminohydroxypropyl ether, and the like; a vinyldiethylaminevinyl acetate copolymer; polyvinyldiethylaminoaceto acetal; polydiethylaminomethylstyrene; polyvinyl pyridine and a copolymer of a vinyl monomer and vinyl pyridine; and vinyl derivatives.

Furthermore, such materials as being swelled by acid, such as Nylon, etc., may also be used.

The microcapsules used in this invention may be prepared by the following way.

Almost all of the shells for capsules prepared by known encapsulation methods are regarded as semipermeable membranes (see, A. Kondo, Microcapsules, published by Nikkan Kogyo Shinbun Sha on April 1970). For instance, the shell material for capsules used in the process disclosed in the specification of French Patent No. 1,362,935 is semipermeable and such capsules are unsuitable for the purpose of this invention.

That is to say, such compounds as having semipermeable property are not used as the materials for capsules in the present invention. The capsule shell made of a non-permeable material in this invention has a thickness of more than few microns, preferably more than 5 microns and is required to have no pin holes.

As the process for making the capsules used in this invention, the processes described in the specifications of Japanese Patent Application Nos. 3042/1969 corresponding to U.S. Pat. No. 3,691,090, 62, 738/1969, corresponding to U.S. Pat. No. 3,703,576 and Japanese Patent Publication No. 9836/1971; and 9382/1970 corresponding to British Patent No. 1,338,151 or Canadian Patent NO. 923,384 or U.S. Pat. No. 3,714,065 are particularly suitable. By the processes disclosed in these specifications; and acid or an alkali as the core material to be encapsulated is dispersed or dissolved in a solution of the polymer usuable under the conditions in this invention, the solution or dispersion is further dispersed by emulsification in a concentrated aqueous salt solution capable of salting out the solution or (high boiling) solvent of low vaper pressure which does not substantially dissolve the both components as liquid paraffin, and then the solvent for the polymer is evaporated away under a reduced pressure or by heating to provide capsules.

The particle sized of the capsules used in this invention are generally from 10 microns to 1 centimeter but capsules having other sizes than above may of course by used in accordance with conditions to be employed. From the view point of easiness in handling or removal and of uniform progress of the buffering action, however, the use of capsules having sizes of from 100 microns to few milimeters is particularly profitable. The content of the acid or the alkali as the core material in capsule may be desirably selected by the conditions employed. A better understanding of the present invention will be attained from the following examples, which are merely intended to be illustrative and not limitative of the present invention.

The invention is illustrated by the following examples.

EXAMPLE 1.

15 g of cellulose acetatephthalate (made by Wako Pure Chemical Industries, Ltd.) was dissolved in 125 ml of acetone and 35 g of oxalic acid powder having a size of from 50 microns to 200 microns was dispersed in the solution. Thereafter, the dispersion was added with stirring to 600 ml of aqueous solution of 40% ammonium sulfate having a pH of 1.0 and having dispersed therein 30 g of starch. By elevating the temperature of the system to 40°C under a slightly reduced pressure and stirring the system for 4 hours under the same condition, 42 g. of cellulose acetate phthalate capsules having particle sizes of from 200 microns to 700 microns and having filled therein oxalic acid were obtained. The capsules were collected, washed thoroughly with water to remove salts and acid attached to the surfaces of the capsules, and then dried.

Figure 2:
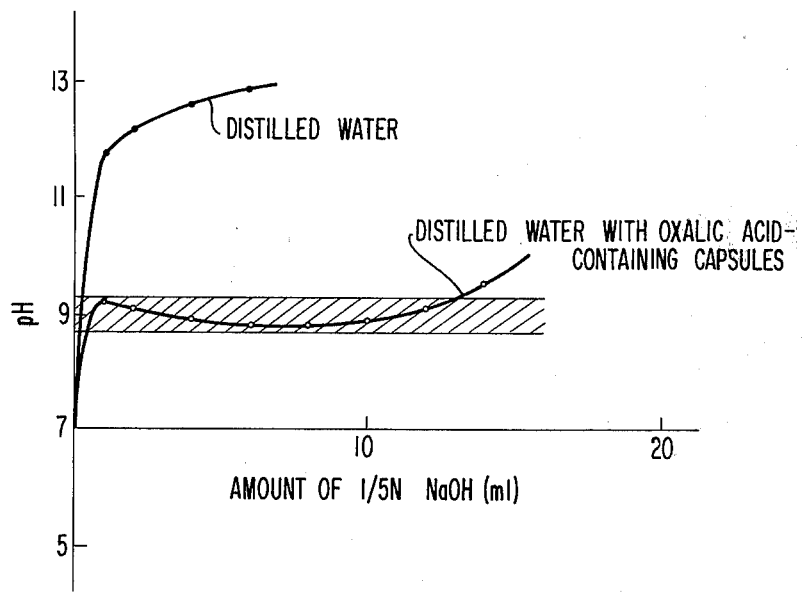

When 2.0 g of the oxalic acid-containing capsules of cellulose acetate phthalate were dispersed in 150 ml of distilled water, the pH of the aqueous system was not varied. Then, while stirring the dispersion at a temperature of 35°C, a 1/5 normal aqueous sodium hydroxide solution was added dropwise to the dispersion at a rate of 1.9 g/min, during which the variation of the pH of the system was recorded. The results are shown in FIG. 2. As shown in FIG. 2, the pH value of the aqueous solution was maintained at a constant value of 9 in a deviation range of 0.3 in pH unit by the presence of the capsules until 13 ml of the 1/5 normal sodium hydroxide solution was added.

The variation of the pH value in the presence of the capsules in accordance with this invention differed clearly from the control case shown in the figure, in which distilled water was used in place of the capsule dispersion.

EXAMPLE 2.

1.5 g of shellac was dissolved in 40 ml of iso-propanol and 8.5 g of sulfamic acid having diameters of shorter than 200 microns was dispersed in the solution. Then, the dispersion was added with stirring to 300 ml of aqueous 40% ammonium sulfate solution.

By elevating the temperature of the system to 40°C under a slightly reduced pressure and stirring continuously the system for 2 hours, 9.5 g of shellac capsules having filled therein sulfamic acid and having diameters of 100 microns to 500 microns were obtained. The capsules were collected and dried as in Example 1.

When 1 g of the capsules thus dried were dispersed in 100 ml of distilled water, the pH value of the aqueous system was not substantially varied. When 1/10 normal sodium carbonate soluiton was added dropwise to the solution, the buffering action was observed.

EXAMPLE 3.

2.0 g of cellulose acetate di-n-butylaminohydroxy propyl ether (made by Wako Pure Chemical Industries, Ltd.) (hereinafter, called CABP) was dissolved in 50 ml of acetone and then 8 g of sodium carbonate monohydrate having particle sizes of less than 200 microns was dispersed in the solution. The dispersion was added with stirring to 300 ml of aqueous 50% magnesium chloride solution having a pH of 13. By elevating the temperature of the system to 40°C under a slightly reduced pressure and stirring the system continuously for 3 hours, 7.5 g of CABP capsules having filled therein sodium carbonate and having diameters of 100 microns to 500 microns were obtained. The capsules were collected and dried as in Example 1. When 1 g of the capsules thus, obtained were dispersed in 100 ml of distilled water, the pH value of the system was not substantially changed. When 5 ml of 1/10 normal hydrochloric acid was added to the system, the buffering action was observed.

EXAMPLE 4.

3g of cellulose acetate phthalate was dissolved in 50 ml of acetone and a sol prepared by impregnating 3 g of silica gel powder having grain sizes of from 5 microns to 20 microns with 5 g of formic acid was dispersed in the solution. Then, the dispersion thus prepared was added with stirring to 300 ml of liquid paraffin cooled to 5°C. By elevating the temperature of the system to 40°C under a slightly reduced pressure and stirring the system continuously for 3 hours, 10.9 g of capsules having filled therein silica gel powder impregnated with formic acid having sizes of 500 microns to 800 microns were obtained. The capsules gave the buffering action as in Example 1-3.

EXAMPLE 5.

2.0 g of the formic acid-containing capsules of cellulose acetate phthalate obtained in Example 4 and 2.0 g of the sodium carbonate-containing capsules of CABP obtained in Example 3 were dispersed together in 100 ml of distilled water. The pH of the system was 6.5. When 2 ml. of 1/10 normal sodium carbonate solution was added dropwise to the dispersion with stirring, the pH of the system was increased but when few milliliters of the solution was added further to the system, the pH of the system was not varied. Then, when 6 ml of 1/10 normal hydrochloric acid was added to the system, the pH of the system was changed to 5.5 but when few milliliters of the hydrochloric acid solution was added further to the system, the pH of the system was not substantially changed.

Although the present invention has been adequately described in the foregoing specification and examples included therein, it is readily apparent that various changes and modifications may be made without departing from the spirit and scope thereof.

What is claimed is:

1. A method for controlling the hydrogen ion concentration of an aqueous alkali solution which comprises adding to the aqueous alkali solution an aqueous solution containing a dispersion of microcapsules prepared by encapsulating an acid material with a polymer which is non-permeable prior to attack by alkali, said polymer being swelled in an alkali state only, the term "swelled" meaning the attacking of said polymer by said solution so that the microcapsule shell is swelled to increase the permeability thereof and thus permit part of the acid within said microcapsule to be released into the solution to neutralize alkali present.

2. A method for controlling the hydrogen ion concentration of an aqueous acidic solution which comprises adding to the aqueous acidic solution an aqueous solution containing a dispersion of microcapsules prepared by encapsulating an alkali material with a polymer which is non-permeable prior to attack by acid, said polymer being swelled in an acid state only, the term "swelled" meaning the attacking of said polymer by said solution so that the microcapsule shell is swelled to increase the permeability thereof and thus permit part of the alkali within said microcapsule to be released into the solution to neutralize acid present.

3. The method of claim 1 wherein said polymer, which is swelled with water in alkaline state only is a member selected from the group consisting of cellulose acetate phthalate, ethylhydroxy ethyl cellulose, hydroxyprophyl methyl cellulose phthalate, starch acetate phthalate, a copolymer of a vinyl monomer and maleic anhydride, a methyl acrylatemethacrylic acid copolymer, a styrene-acrylic acid copolymer, and polyvinyl acetate phthalate.

4. The method of claim 2, wherein said acid material is a member selected from the group consisting of sulfuric acid, hydrochloric acid, nitric acid, sulfamic acid, formic acid, phosphoric acid, oxalic acid, succinic acid, citric acid, sodium phosphate, and potassium phosphate.

5. The method of claim 1, wherein said alkaline material is a member selected from the group consisting of sodium hydroxide, potassium hydroxide, sodium carbonate, sodium bicarbonate, di-sodium phophate, di-potassium phosphate, n-dibutylamihne, and trihydroxymethylamino methane.

6. The method of claim 2, wherein said polymer, which is swelled with water in the acid state only is a member selected from the group consisting of diethylaminomethyl cellulose, cellulose acetate, N,N-di-n-butylaminohydroxypropyl, a vinyldiethylamine-vinyl acetate copolymer, polyvinyldiethylaminoaceto acetal, polydiethylaminomethyl styrene, polyvinyl pyridine, copolymers of a vinyl monomer and vinyl pyridine, and nylon.

7. The method of claim 1, in which said polymer which is swelled with water in the alkaline state only is replaced with a high molecular weight material selected from the group consisting of shellac and casein resin.

8. The process of claim 1 wherein the acid material encapsulated with the polymer is citric acid.

9. The process of claim 2 wherein the alkali material encapsulated by said polymer is selected from the group consisting of sodium carbonate and sodium bicarbonate.

10. The process of claim 1 wherein the microcapsules have a particle size of 10 microns to 1 centimeter.

11. The process of claim 2 wherein the microcapsules have a particle size of 10 microns to 1 centimeter.

12. A method for controlling the hydrogen ion concentration of an aqueous alkali solution which comprises adding to the aqueous alkali solution an aqueous solution containing a dispersion of microcapsules prepared by encapsulating an acid material with a polymer which is non-permeable prior to attack by alkali, said polymer being swelled in an alkali state only, the term "swelled" meaning the attacking of said polymer by said solution so that the microcapsule shell is swelled to increase the permeability thereof and thus permit part of the acid within said microcapsule to be released into the solution to neutralize alkali present, said polymer being cellulose acetate phthalate.

13. A method for controlling the hydrogen ion concentration of an aqueous alkali solution which comprises adding to the aqueous alkali solution an aqueous solution containing a dispersion of microcapsules prepared by encapsulating an acid material with a polymer which is nonpermeable prior to attack by alkali, said polymer being swelled in an alkali state only, the term "swelled" meaning the attacking of said polymer by said solution so that the microcapsule shell is swelled to increase the permeability thereof and thus permit part of the acid within said microcapsule to be released into the solution to neutralize alkali present, said polymer being a casein resin.

14. A method for controlling the hydrogen ion concentration of an aqueous acidic solution which comprises adding to the aqueous acidic solution an aqueous solution containing a dispersion of microcapsules prepared by encapsulating an alkali material with a polymer which is nonpermeable prior to attack by acid, said polymer being swelled in an acid state only, the term "swelled" meaning the attacking of said polymer by said solution so that the microcapsule shell is swelled to increase the permeability thereof and thus permit part of the alkali within said microcapsule to be released into the solution to neutralize acid present, said polymer being N,N-di-n-butylamino hydroxypropyl ether.

15. A method for controlling the hydrogen ion concentration of an aqueous alkali solution which comprises adding to the aqueous alkali solution an aqueous solution containing a dispersion of microcapsules prepared by encapsulating citric acid with a polymer which is nonpermeable prior to attack by alkali, said polymer being swelled in an alkali state only, the term "swelled" meaning the attacking of said polymer by said solution so that the microcapsule shell is swelled to increase the permeability thereof and thus permit part of the acid within said microcapsule to be released into the solution to neutralize alkali present, said polymer being cellulose acetate phthalate.

16. A method for controlling the hydrogen ion concentration of an aqueous alkali solution which comprises adding to the aqueous alkali solution an aqueous solution containing a dispersion of microcapsules prepared by encapsulating citric acid with a polymer which is non-permeable prior to attack by alkali, said polymer being swelled in an alkali state only, the term "swelled" meaning the attacking of said polymer by said solution so that the microcapsule shell is swelled to increase the permeability thereof and thus permit part of the acid within said microcapsule to be released into the solution to neutralize alkali present, said polymer being a casein resin.

17. A method for controlling the hydrogen ion concentration of an aqueous acidic solution which comprises adding to the aqueous acidic solution an aqueous solution containing a dispersion of microcapsules prepared by encapsulating an alkali material selected from the group consisting of sodium carbonate and sodium bicarbonate with a polymer which is nonpermeable prior to attack by acid, said polymer being swelled in an acid state only, the term "swelled" meaning the attacking of said polymer by said solution so that the microcapsule shell is swelled to increase the permeability thereof and thus permit part of the alkali within sid microcapsule to be released into the solution to neutralize acid present, said polymer being N,N-di-n-butylamino hydroxypropyl ether.

* * * * *